Aug. 31, 1965 O. SPRING Plant Pat. 2,551

VARIETY OF CREPE MYRTLE

Filed Oct. 30, 1963

Inventor

Otto Spring

United States Patent Office

Plant Pat. 2,551
Patented Aug. 31, 1965

2,551
VARIETY OF CREPE MYRTLE

Otto Spring, Okmulgee, Okla., assignor to Howard Corley and Al Houchin, both of Tulsa, Okla.

Filed Oct. 30, 1963, Ser. No. 320,243
1 Claim. (Cl. Plt.—54)

This invention relates to a new and improved crepe myrtle plant, the principally new and different characteristics of which are the distinctive strong purplish pink, as shown by the Nickerson Color Fan—7.5 R.P.—7/10, flower heads, very dwarf habit of growth, and exceptionally long and prolific blooming quality. The crepe myrtle was derived of a long-line breeding program from a hybridizing of *Lagerstroemia indicia* and *Lagerstroemia reginae*. The crepe myrtle is distinguished by the characteristics mentioned. The new variety of crepe myrtle has been asexually reproduced at Okmulgee, Oklahoma, by both hardwood and softwood stem cuttings which retain the characteristics of the parent.

The accompanying drawings show a typical flower head, its color and the compact dwarf growth habit of a typical plant.

Figure 2:
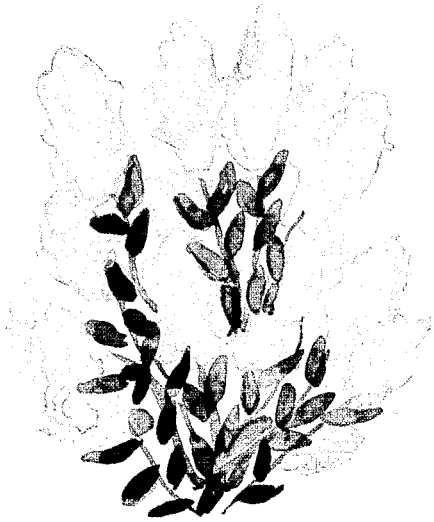
FIGURE 2 is a sketch in full color illustrating the general form and arrangement of a typical bush, or full plant.
Figure 1:
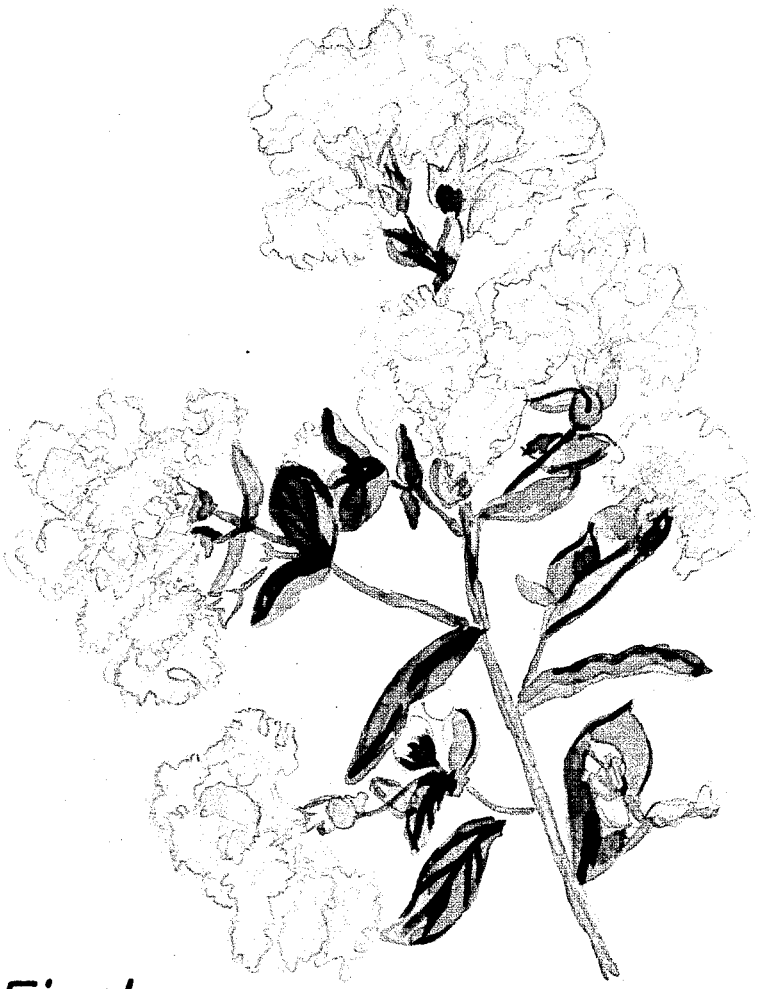
FIGURE 1 is a view in full color showing one flower head with a detailed drawing of the foliage and wood, together with buds and fully matured flowers.

A detailed description of this new variety of crepe myrtle follows:

*Habit of growth*

Compact, bushy, maturing at 16 to 24 inches when pruned back close to ground level in early spring, growing from 6–8 inches yearly thereafter.

*Foliage*

Foliage is heavy, of a good green color, with leaves approximately 1 inch long, simple, entire, with fairly short petioles.

*Flower heads*

Terminal inflorescence, compact, pyramidal shaped and longer lasting than common crepe myrtle flower heads. Latter part of the growing season, seed pods (fruits), full open blooms and unopened buds may be found on the same inflorescence.

*Flower*

The arrangement of the floral parts and the shape of the six petals on each flower are the same as the common crepe myrtle, *Lagerstroemia indicia*. The flowers are strong purplish pink, as shown by the Nickerson Color Fan—7.5 R.P.—7/10, and approximately one-half inch long.

Blooming habit: Continuous blooming season for this variety at Okmulgee, Oklahoma, is normally from mid-June through September. The long bloom progression of this crepe myrtle is because of the development of new flower buds on the pedicel after either the bloom fails to pollinate or the seed capsule begins to mature. Flowers open a strong purplish pink, as shown by the Nickerson Color Fan—7.5 R.P.—7/10, and remain the same color unless rained upon.

Ovary: Pale green, smooth, ¼ inch long.

Sepals: Pale green, small.

Stamens: Slender, extended, approximately 1 inch long, 18 normally per flower, pale yellow color.

Pistil: Averages ⅜ inch long, stigma pale yellow.

Buds: Ovoid in shape, ¼ inch diameter.

Ripened fruits: ¼ inch diameter by ⅜ inch long, calyx persistent. Ten locules comprise interior. Exterior brown and woody.

*Parentage*

Offspring of two unnamed breeding lines developed by the inventor during the past 27 years.

It is recognized that the plant will vary somewhat with the season, planted in different areas, and under different growing conditions, although it will nevertheless retain its distinctive characteristics and properties.

Having thus disclosed my discovery, I claim:

The new and distinct variety of crepe myrtle plant herein described and illustrated, characterized by the distinctive strong purplish pink color as shown by the Nickerson Color Fan—7.5 R.P.—7/10, a natural dwarf habit of growth, and long and prolific blooming habit.

No references cited.

ABRAHAM G. STONE, *Primary Examiner.*